(12) United States Patent
Kato et al.

(10) Patent No.: US 8,918,944 B2
(45) Date of Patent: Dec. 30, 2014

(54) INTERDENTAL BRUSH

(75) Inventors: Keisuke Kato, Osaka (JP); Shinya Sakurai, Osaka (JP)

(73) Assignee: Sunstar Inc., Takatsuki-shi (JP)

( * ) Notice: Subject to any disclaimer, the term of this patent is extended or adjusted under 35 U.S.C. 154(b) by 91 days.

(21) Appl. No.: 13/120,245

(22) PCT Filed: Sep. 25, 2009

(86) PCT No.: PCT/JP2009/066663
§ 371 (c)(1),
(2), (4) Date: Mar. 22, 2011

(87) PCT Pub. No.: WO2010/038678
PCT Pub. Date: Apr. 8, 2010

(65) Prior Publication Data
US 2011/0173766 A1    Jul. 21, 2011

(30) Foreign Application Priority Data

Sep. 30, 2008  (JP) ................................. 2008-253153

(51) Int. Cl.
| A46B 9/04 | (2006.01) |
| A46B 3/18 | (2006.01) |
| A46D 1/00 | (2006.01) |
| A61C 15/02 | (2006.01) |

(52) U.S. Cl.
CPC ... *A46B 3/18* (2013.01); *A46D 1/00* (2013.01); *A46D 1/0238* (2013.01); *A46B 2200/108* (2013.01); *A61C 15/02* (2013.01)
USPC ............................ 15/167.1; 15/206; 15/207.2

(58) Field of Classification Search
USPC ........................................................ 15/167.1
IPC ..................................... A46B 3/18; A61C 15/00
See application file for complete search history.

(56) References Cited

U.S. PATENT DOCUMENTS

| 4,632,136 | A | * | 12/1986 | Kingsford | ...................... 132/218 |
| 4,927,281 | A | * | 5/1990 | Gueret | ........................... 401/129 |
| 5,355,547 | A | * | 10/1994 | Fitjer | ................................ 15/206 |
| 5,882,584 | A | * | 3/1999 | Tsurukawa | ..................... 420/59 |

FOREIGN PATENT DOCUMENTS

| JP | 09-023928 A | 1/1997 |
| JP | 2003-102548 A | 4/2003 |

(Continued)

OTHER PUBLICATIONS

International Search Report of PCT/JP2009/066663, date of mailing Oct. 20, 2009.

*Primary Examiner* — Monica Carter
*Assistant Examiner* — Stephanie Berry
(74) *Attorney, Agent, or Firm* — Westerman, Hattori, Daniels & Adrian, LLP

(57) ABSTRACT

Provided is an interdental brush having a wire and filaments arranged therein by folding the wire and disposing the filaments between the wire and then twisting the wire. The interdental brush has improved filament retention and improved cleaning effectivity and reachability to minute portions. Each of filaments 3 has a polygonal cross section whose at least one corner portion has an interior angle 31 as acute as 30 to 75 degrees. Specifically, an angle θ3 of the acute corner portion 31 is set at 1.2 to 3 times a twisting angle θ4 of the wire. The filaments each have two or more such acute corner portions, and two or more rows of such filaments are disposed and laminated between the wire in a densely arranged manner.

18 Claims, 7 Drawing Sheets

(56) References Cited

FOREIGN PATENT DOCUMENTS

| | | | | |
|---|---|---|---|---|
| JP | 2004/188081 | * | 7/2004 | ............. A46D 1/055 |
| JP | 2004-188081 A | | 7/2004 | |
| JP | 2004188081 | * | 7/2004 | ............... A46D 1/55 |
| JP | 2006-158773 A | | 6/2006 | |
| JP | 2006-254954 A | | 9/2006 | |
| JP | 2008012125 A | * | 1/2008 | ............... A46D 1/55 |
| JP | 3139296 U | | 2/2008 | |

* cited by examiner (a)

(b)

INTERDENTAL BRUSH

BACKGROUND OF THE INVENTION

1. Technical Field

The present invention relates to interdental brushes with a brush portion having wires and filaments arranged on the periphery of the wires by disposing the filaments between the wires and then twisting the wires, and particularly to an interdental brush with improved filament retention, in addition to superior cleaning effectivity and reachability to minute portions.

2. Background Art

Conventionally, various proposals have been made for this kind of interdental brushes. For example, Japanese Unexamined Patent Application No. 9-23928 proposes an interdental brush with a bristle arranged portion having two or more sections wherein adjacent sections arrange therein filaments of mutually different physical properties (material, hardness, thickness, color, and the like), thereby implementing a variety of required functions on a single interdental brush or implementing an interdental brush that provides for proposals for new applications with newly added functions. Japanese Registered Utility Model Publication No. 3139296 proposes an interdental brush wherein the filaments on the brush portion have formed thereon a plurality of depressions, thereby providing the interdental brush with improved interdental insertibility and cleanability, good comfortability, and superior durability. However, these conventional interdental brushes have been faced with some degree of limitation in improving the brush portion in respect of its cleaning effectivity and reachability to minute portions of teeth such as interdental corners.

SUMMARY OF THE INVENTION

Problems to be Solved by the Invention

In view of the foregoing and other circumstances, it is an object of the present invention to provide an interdental brush with improved cleaning effectivity and reachability to minute portions and improved filament retention.

Means of Solving the Problems

As a result of an extensive study in an attempt to solve the above-described problems, the present inventors have found that the conventional interdental brushes have limited cleanability and limited reachability to minute portions, as detailed below, because the filaments used on the brush portion have circular cross sections. The present invention has been made to solve this problem.

A possible way to enhance the cleaning effectivity of interdental brushes is to increase the filling density of the arranged filaments. With the conventional filaments of circular cross sections, no matter how densely they are disposed between wires during production, the circular nature causes spaces to be formed between the filaments and between the filaments and the wires when the filaments are in an arranged state after twisting the wires. Thus, there is some degree of limitation to the improvement of the filling density. Because of the spaces there is a limited friction force, which might cause the filaments to come off during cleaning. In addition, the part contributory to the cleaning effectivity during interdental cleaning is not the tips of the filaments as in toothbrushes but side portions (peripheries) of the filaments, which bend when interdentally inserted and come into contact with interdental portions of teeth. In this regard, the filaments of circular cross sections form arcs at the side portions and thus have limited effects of wiping out dirt and limited reachability to minute portions as well. Although use of thin filaments would provide for reachability to minute portions even with circular cross sections, such filaments are weak in resistant strength, resulting in degraded cleaning effectivity.

The present invention provides an interdental brush including a brush portion having a wire and filaments arranged therein by folding the wire and disposing the filaments between the wire and then twisting the wire, wherein the filaments each have a polygonal cross section, and at least one interior angle of the polygonal cross section has an acute angle of 30 to 75 degrees. The "acute angle" encompasses cases of somewhat round corner tips while securing an acute internal angle between two sides. The "polygon" encompasses polygons of somewhat round corner portions and of somewhat distorted shapes such that a side protrudes somewhat outwardly or depresses inwardly. The polygonal cross section preferably has two or more acute corner portions.

The acute angle is preferably 1.2 to 3 times the twisting angle of the wire. The "twisting angle of the wire" means an angle of the wire relative to the axial direction of the formed brushed portion (i.e., the direction of interdental insertion of the brush portion), and the filaments disposed between the wire are arranged spirally along the twisting angle.

Preferably, two or more rows of the arranged filaments between the wire are laminated in the axial direction of the brush portion. A "row" of the filaments between the wire means that the filaments are arranged in a line along the longitudinal direction of the wire with the cross sections of the filaments facing in the same directions. The "laminated state" means that two or more of such rows are laminated in the wire width direction, which is orthogonal to the wire longitudinal direction. The "axial direction of the brush portion" means the direction of insertion or pulling out of the interdental brush.

Preferably, the filaments are laminated with their polygonal cross sections in a densely arranged state. The "densely arranged state" means that the polygonal cross sections of the filaments are densely arranged without spaces, but the state encompasses cases where spaces exist to some degree. It should be noted that not all of the polygonal cross sections of the filaments arranged in the brush portion need to be densely arranged; at least half the arranged filaments need to be densely arranged. Arranging the filaments in a dense and laminated state causes two adjacent filaments to form an approximately parallelogramic cross section.

Effects of the Invention

With such interdental brush according to the present invention, making the cross section of each filament polygonal such as an equilateral triangle enables the acute corner portion of the polygonal cross section to be oriented in the axial direction of the brush portion (the direction of insertion or pulling out of the interdental brush) when the filaments are disposed between the wire and then the wire is twisted. This concentrates the brushing pressure on the acute corner portion during wiping, thereby improving the cleaning effectivity, and enables the acute portion to reach interdental posterior portions of teeth, thereby making it possible to uproot dirt. With filaments having the cross section according to the present invention, the wire is filled with the filaments with the sides of the polygonal cross sections in close contact with each other, resulting in a structure of increased filament density. This makes the filaments hard to come off from the wire because of the friction force and the like, compared with conventional filaments of circular cross sections. The present invention secures superior cleaning effectivity particularly when the filament cross section is an approximately equilateral triangle, an approximate rhombus, an approximate isosceles triangle, or an approximate parallelogram, in which case the wire can be most densely filled with two or more rows of the filaments. Among the foregoing, filaments of approximately equilaterally triangular cross sections are particularly superior in cleaning effectivity, have high filament resistant strength and a high filling rate of arrangement, and reduce the failure rate during production.

BRIEF DESCRIPTION OF THE DRAWINGS

FIG. 3A shows an example of lamination of four rows of filaments of approximately equilateral cross sections, and FIG. 3B shows an example of lamination of two rows of such filaments.

FIG. 6A shows an example of lamination of two rows of filaments, and FIG. 6B shows an example of lamination of one row of filaments.

DETAILED DESCRIPTION OF THE INVENTION

An embodiment of the present invention will be described in detail on the basis of the appended drawings.

Figure 1:
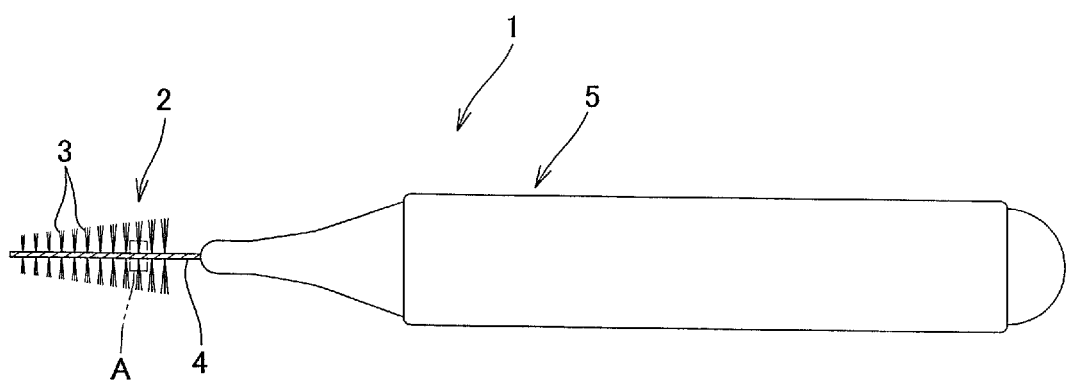
FIG. 1 is a diagram illustrating an entire configuration of an interdental brush according to a representative embodiment of the present invention.

FIG. 1 is a diagram illustrating an entire configuration of an interdental brush according to the present invention, where reference numeral 1 denotes an interdental brush, 2 denotes a brush portion, 3 denotes filaments, 4 denotes a wire, and 5 denotes a handle portion.

Figure 2:
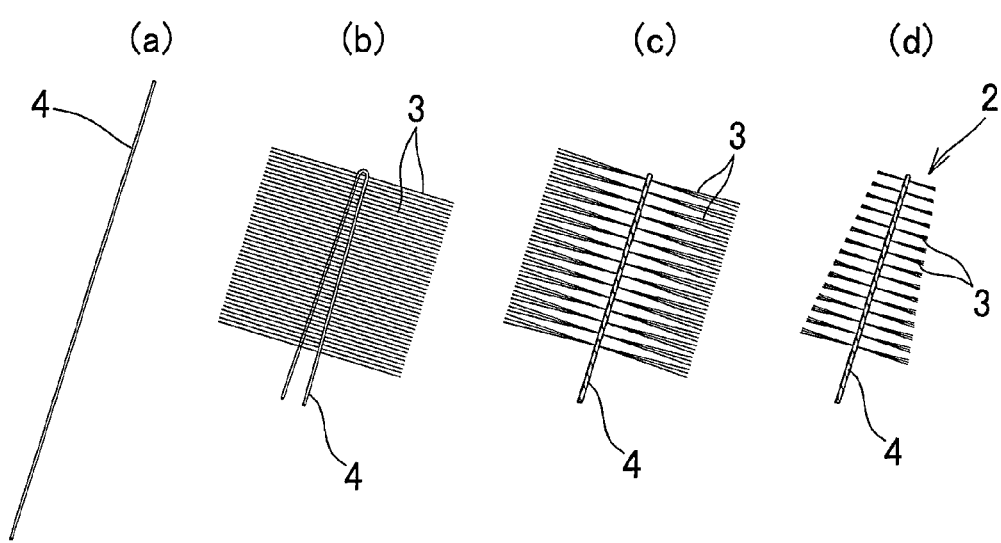
FIGS. 2A to 2D are diagrams illustrating a procedure of production of a brush portion.

Referring to FIGS. 1 and 2, an interdental brush 1 includes a brush portion 2 having a wire 4 and a plurality (multiplicity) of filaments 3 arranged radially on the periphery of the wire 4 by folding the wire 4 and disposing the filaments 3 between the wire 4 and then twisting the wire 4, followed by bristle cutting for shaping. In particular, the present invention is characterized in that the filaments 3 each have a polygonal cross section and that at least one interior angle of the polygon has an acute angle of 30 to 75 degrees, thereby improving filament retention as well as significantly improving the cleanability of interdental portions of teeth and reachability to minute portions compared with conventional interdental brushes that arrange filaments of circular cross sections.

Figure 7:
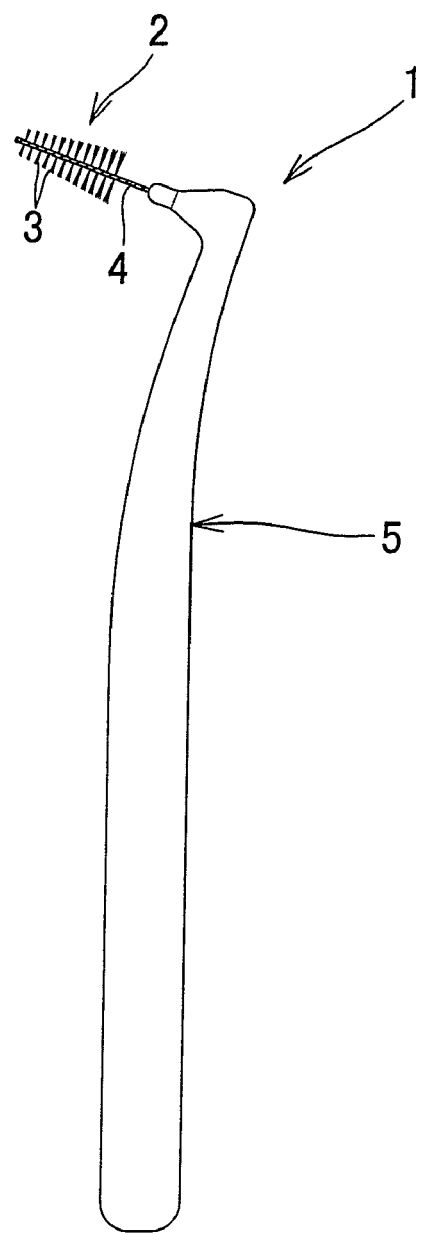
FIG. 7 is a diagram illustrating a modified example of a handle portion of the interdental brush.

In this example, a wire base of the brush portion 2 is embedded in the tip of a bar-shaped handle portion 5 of synthetic resin. Examples of the method of holding the brush portion 2 on the handle portion 5 include: inserting a prepared brush portion 2 into the handle portion 5 at the time of molding thereof; and forming an attachment hole on the handle portion 5 and inserting the wire base into the attachment hole after heating the wire base by high frequency heating, ultrasonic fusion, or the like. The brush portion 2 may be detachably inserted into the attachment hole of the handle portion 5 instead of being fixed thereto. Alternatively, the handle portion 5 may be bent at the tip in the form of L and the brush portion 2 may protrude from the tip, as shown in FIG. 7. Other examples include a disposable type in which the brush base of the brush portion 2 is embedded in and fixed to a short axis handle, a type in which a long axis holder detachably holds a short axis base that embeds therein and fixes thereto the brush base of the brush portion 2, a type in which the tip of the long axis holder is bent, and a type in which the long axis holder is a motor-driven interdental brush. Thus, various forms are possible.

As the material of the filament 3 and the wire 4, which constitute the brush portion 2, conventionally well-known materials may be used. The filament 3 is a mono-filament of synthetic resin and may be conveniently selected from polyamide (nylon), polypropylene, polyethylene, polyethylene terephthalate (PET), polybutylene terephthalate (PBT), polytrimethylene terephthalate (PTT), mixtures of the foregoing resins, and other synthetic resins. The filament 3 may contain fine particles or chemicals. As the wire 4, a stainless steel wire of SUS304, SUS316, or the like may be conveniently used. For example, a stainless steel wire containing a large quantity of manganese is preferable, and it is also possible to use a cobalt alloy or the like.

As the method of arranging the filaments 3 into the wire 4, various conventionally well-known methods may be used. An example is a picking method, which includes: placing a picker with grooves formed at predetermined intervals onto an original bunch of several hundreds of filaments of a predetermined length, thereby picking a predetermined number of filaments into the grooves; disposing the filaments between a wire; and twisting the wire. Another example is a reeling method, which includes: preparing a winder by winding a continuous bristle bunch of a plurality of filaments on a reel; disposing a plurality of such winders in parallel; supplying the space between the wire with a group of bristle bunches that are simultaneously pulled out of the plurality of winders while evenly dispersing the bristle bunches over the space between the wire; and twisting the wire. The bristle shape of the brush portion 2 after arranging may be that of a cone as shown in FIG. 1 or various other shapes such as that of a cylinder, a barrel, and a drum.

Figure 3:
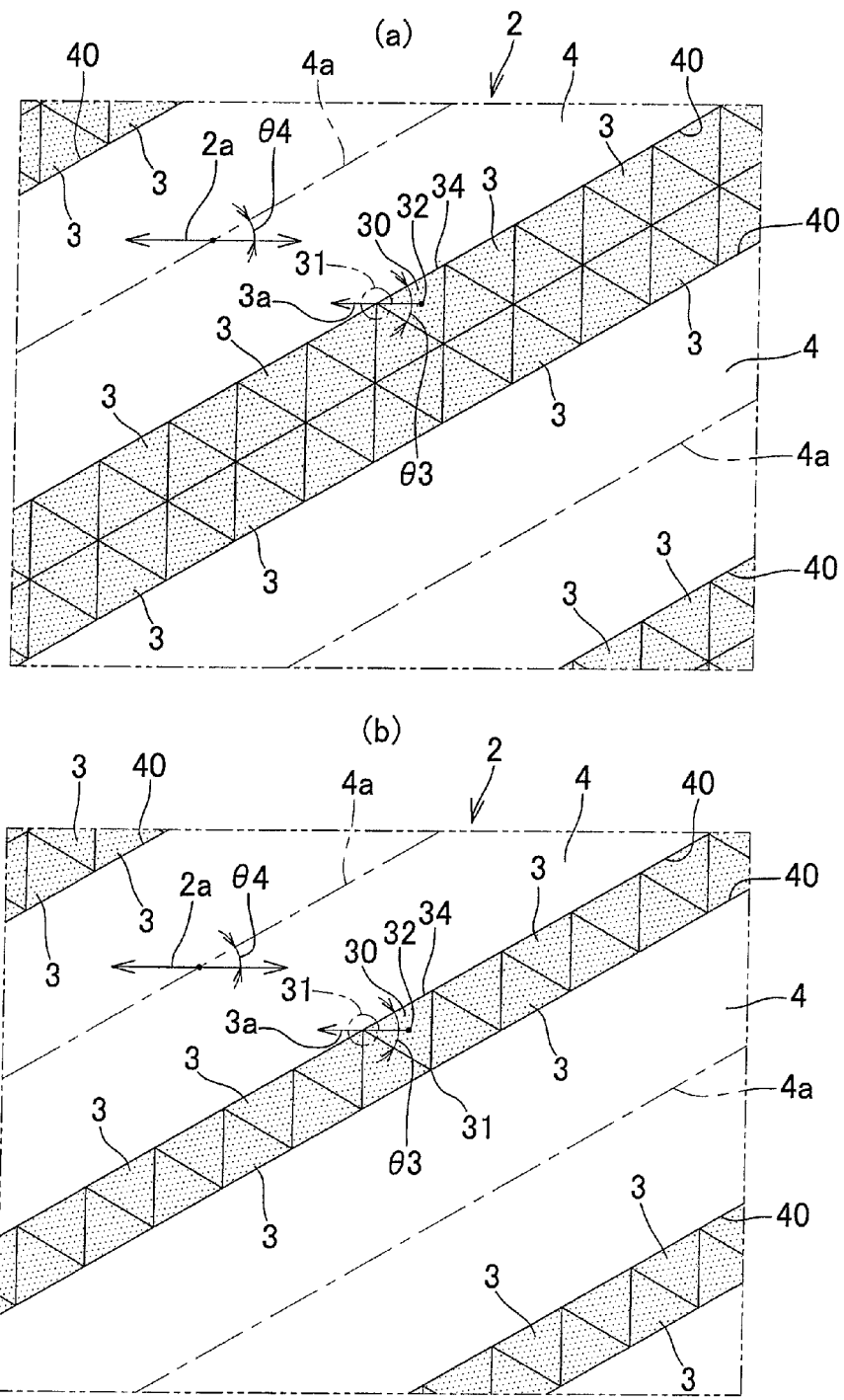
FIGS. 3A and 3B are enlarged schematic diagrams (illustrating diagrams) of filaments of approximately equilaterally triangular cross sections arranged between wires.
Figure 4:
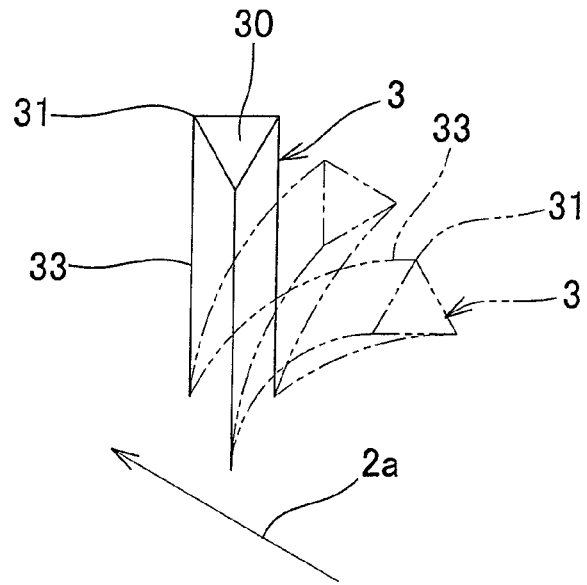
FIG. 4 is a diagram illustrating behavior of a filament during interdental cleaning.
Figure 5:
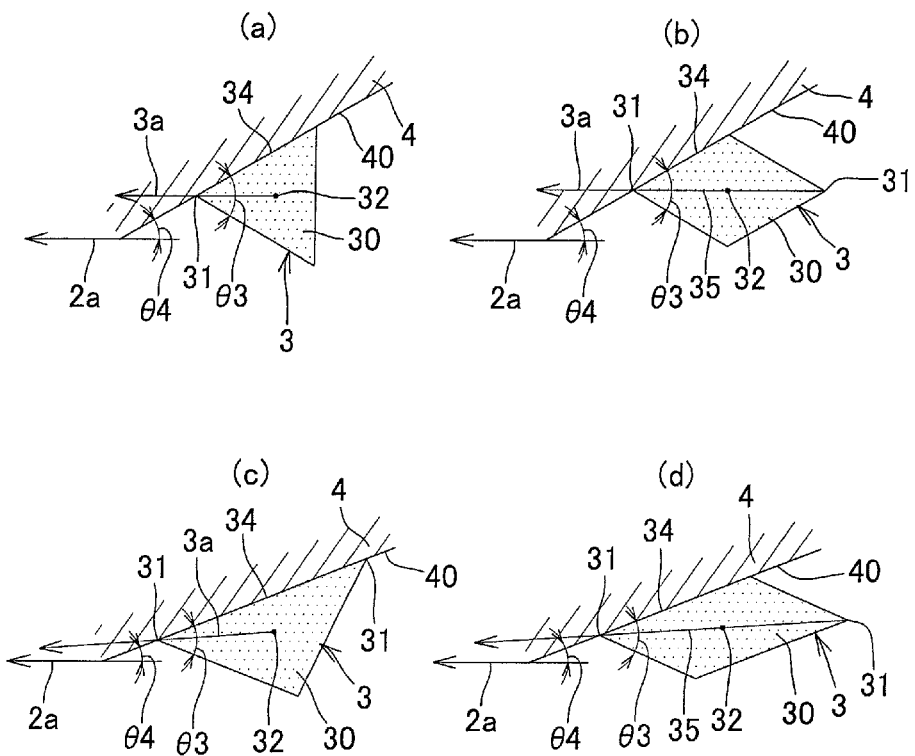
FIGS. 5A to 5D are diagrams illustrating preferred examples of the filament cross section.

Referring to FIGS. 3A and 3B, which show on an enlarged the space between the wire at A indicated in FIG. 1, the filaments 3 are arranged between the wire 4 spirally along the twisting direction of the wire 4, with the arrangement of the filaments 3 controlled at one row or more than one rows depending on the number of the disposed filaments or the twisting conditions of the wire. For example, with 200 to 500 filaments disposed between the wire, the number of times of twisting the wire at the filament disposed portion (the winding number of times) may be set at 10 to 20 times, thereby enabling the arrangement of the filaments to be controlled at 10 to 55 filaments arranged per unit twisting number of the wire (per one twist), preferably at 15 to 40 filaments, and more preferably at 20 to 35 filaments. FIG. 3A shows an example of lamination of four rows of filaments of approximately equilateral cross sections, and FIG. 3B shows an example of lamination of two rows of such filaments. In the present invention, each filament 3 has a polygonal cross section 30, and at least one interior angle of the polygon has an acute angle of 30 to 75 degrees, preferably 45 to 70 degrees, and more preferably 50 to 70 degrees. This makes an orientation 3a of an acute corner portion 31 of a filament cross section 30, which is viewed from a center of gravity 32, approximately equal or close to an axial direction (insertion direction) 2a of the brush portion 2, when the filaments 3 are disposed between the wire, as also shown in FIG. 5A. This in turn enables a ridge portion 33 at the acute angle shown in FIG. 4 to easily reach interdental corners during cleaning and thus uproot accumulated dirt, thereby significantly improving the cleaning effectivity. This also increases the filament resistant strength because of structural advantages, resulting in enhanced bristle hardness and elasticity.

It is effective that the orientation 3a of the acute corner portion 31 of each of thus arranged filaments 3 is approximately equal to the axial direction 2a of the brush portion 2. This requires an angle θ3 of the corner portion 31 to be larger than a twisting angle θ4 of the wire. More specifically, the angle θ3 is 1.2 to 3 times, preferably 1.5 to 2.5 times, and more preferably 1.7 to 2.2 times the twisting angle θ4. At an angle θ3 of equal to or smaller than the twisting angle θ4, the filaments easily fall down laterally during cleaning, resulting in degraded resistance (hardness and elasticity). An angle θ3 of 1.2 to 3 times the twisting angle θ4 provides the filaments with good stability to prevent them from falling to the right and left easily and thus with increased resistant strength, thereby improving the cleaning effectivity. The twisting angle θ4, which is usually determined by the thickness of the wire and the like, is 25 to 40 degrees, and preferably 30 to 35 degrees.

Before the wire is twisted, the filaments 3 are placed between the wire along with some space, and most of the filaments 3 are in a stable state such that a longest side 34 of the polygonal cross section is along the longitudinal direction of the wire 4, while in the case of a polygonal cross section of four or more corners, most of the filaments 3 are in a stable positional state such that a longest diagonal line 35 is along the longitudinal direction of the wire 4. As the wire 4 with the filaments 3 in this state is twisted to reduce the space, each filament 3 comes into a state of close contact with a periphery 40 of the wire 4, and thus after the twisting, the longest side 34 is in close contact with the wire periphery 40, while the longest diagonal line 35 is in a state close to the spiral direction when the filaments 3 are in close contact with the wire 4. For the orientation 3a of the acute corner portion 31 of each filament 3 to be approximately equal to the axial direction 2a of the brush portion 2, as described above, the acute corner portion 31 preferably constitutes at least one end of the longest side 34 of the polygonal cross section, and such corner portion 31 preferably has an acute angle of 30 to 75 degrees. As used herein, the "longest side" refers to all sides of an approximately equilateral triangle, an approximate rhombus, and the like where all the sides are equal. In the case where there are a plurality of longest sides, the "longest side" refers to any of these sides. The acute corner portion 31 is preferably a corner portion that constitutes the longest diagonal line 35, and more preferably, both corner portions 31 constituting the diagonal line 35 each have an acute angle of 30 to 75 degrees.

Preferably, the specific cross section of each filament 3 is an approximately equilateral triangle, an approximate rhombus, an approximate isosceles triangle, or an approximate parallelogram, as shown in FIGS. 5A to 5D, considering the above-described relationship between the longest side or diagonal line with the corner portion, and further considering the resistant strength and filling density of the filaments during arrangement. It will be readily appreciated that the "approximately equilateral triangle," the "approximate rhombus," the "approximate isosceles triangle," and the "approximate parallelogram" encompass shapes such that corners of an equilateral triangle, a rhombus, an isosceles triangle, and a parallelogram are somewhat round, and distorted shapes such that a side protrudes somewhat outwardly or depresses inwardly. Particularly preferable are the approximately equilateral triangle and the approximate rhombus respectively shown in FIGS. 5A and 5B, in terms of the resistant strength due to an approximate left-right symmetry secured relative to the axial direction 2a of the brush portion 2. A further particularly preferable example is the approximately equilateral triangle, which is a well-balanced equilateral polygon, in various respects including superior cleaning effectivity, a high filling density, high bristle retention, a reduced failure rate during production, and increased resistant strength.

In the case of the approximate isosceles triangle, an obtuse approximate isosceles triangle as shown in FIG. 5C, where both corner portions 31 at both ends of the longest side 34 are acute, is preferable. This increases the filling density as well. Referring to FIGS. 5B and 5D, it is seen that in both cases of the approximate rhombus and the approximate parallelogram, the longer diagonal line 35 is approximately equal to the axial direction 2a of the brush portion 2, thereby improving the cleaning effectivity. In the cases of the approximate rhombus, approximate isosceles triangle, and approximate parallelogram, with the approximately equilateral triangle excluded, the angle θ3 of the acute corner portion 31 is preferably set within the range of 30 to 75 degrees, as described above.

Figure 6:
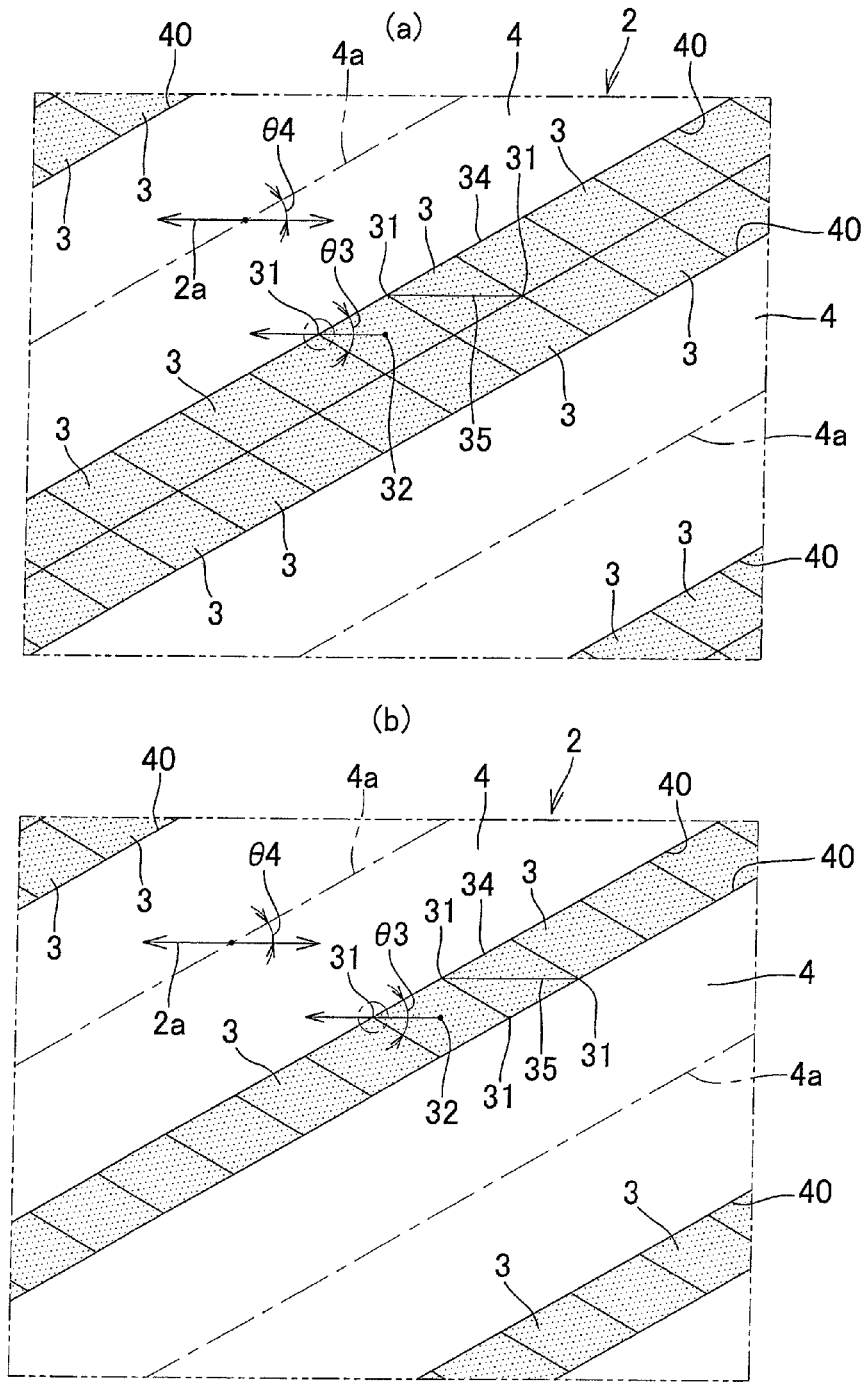
FIGS. 6A and 6B are enlarged schematic diagrams (illustrating diagrams) of filaments of approximately rhombic cross sections arranged between wires.

FIGS. 6A and 6B are enlarged schematic diagrams of arranged filaments of approximately rhombic cross sections: FIG. 6A shows an example of lamination of two rows of filaments, and FIG. 6B shows an example of lamination of one row of filaments. Filling the wire with two or more rows of filaments increases the filling density of the filaments and bristle retention. In addition, the filaments support each other to improve the resistant strength, thereby enhancing the cleaning effectivity.

It should be noted that not all the filaments 3 constituting the brush portion 2 need to have the same cross sections; a plurality of kinds of filaments of mutually different cross sections may be mixed at the time of arranging. Although such filaments may be mixed in a random manner, the same kinds of filaments are preferably arranged collectively in the same areas, considering the filling density. For example, this configuration encompasses the case where the filaments in an arranging area at the distal end side of the wire have approximately rhombic cross sections while the filaments in an arranging area at the base end side have approximately equilaterally triangular cross sections, and the case where filaments of cross sections not encompassed within the present invention such as circular cross sections are mixed in a random manner or in a selected area. It is also possible to use twisted filaments.

While embodiments of the present invention have been illustrated and described, it is not intended that these embodiments limit the present invention. Rather, it is understood that various forms are possible without departing from the scope of the present invention.

EXAMPLES

Next, description will be made of results of a test for cleaning effectivity using samples of the brush portion.
(Wipability Test)
Artificial plaque ("Occlude" in trade name, available from Pascal Company Inc.) was deposited on a portion of an artificial interdental model corresponding to an interdental surface. The artificial plaque was wiped with brush samples of examples 1 to 3 and comparative examples 1 to 3, described below, by inserting and pulling each brush sample into and out of the artificial interdental portion once. After the wiping, the interdental surface of the artificial interdental model was photographed, and the removal percentage of the artificial plaque was calculated by image analysis.

(Brush Samples)

All the brush samples were prepared by using filaments of nylon material and twisting a stainless wire of SUS304. The filament cross section of example 1 was an approximately equilateral triangle, that of example 2 was an approximate isosceles triangle, that of example 3 was an approximate rhombus, that of comparative example 1 was a circle, that of comparative example 2 was a rectangle, and that of comparative example 3 was the same circle as comparative example 1. The filament periphery was smooth in examples 1 to 3 and comparative examples 1 and 2, and rough in comparative example 3.

(Test Results)

Table 1 confirms superior cleaning effectivity of examples 1 to 3 with the removal percentage in excess of 82%, in contrast to lower than 79% in comparative examples 1 to 3. Among examples 1 to 3, example 1, which had an approximately equilaterally triangular filament cross section, showed a high cleaning effectivity of 89.0%.

TABLE I

| Samples | Filament cross section | Filament periphery | Removal percentage (%) |
|---|---|---|---|
| Example 1 | Approximately equilateral triangle | Smooth | 89.0 |
| Example 2 | Approximate isosceles triangle | Smooth | 84.5 |
| Example 3 | Approximate rhombus | Smooth | 82.5 |
| Comparative Example 1 | Circle | Smooth | 78.8 |
| Comparative Example 2 | Rectangle | Smooth | 75.4 |
| Comparative Example 3 | Circle | Rough | 73.6 |

Figure 8:
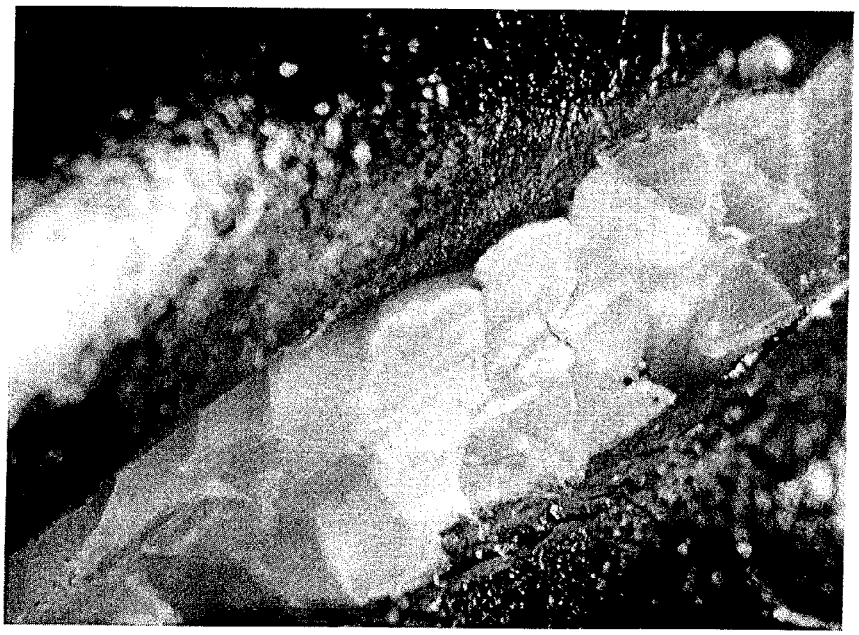
FIGS. 8A and 8B are enlarged photographs of the brush portion.
Figure 8:
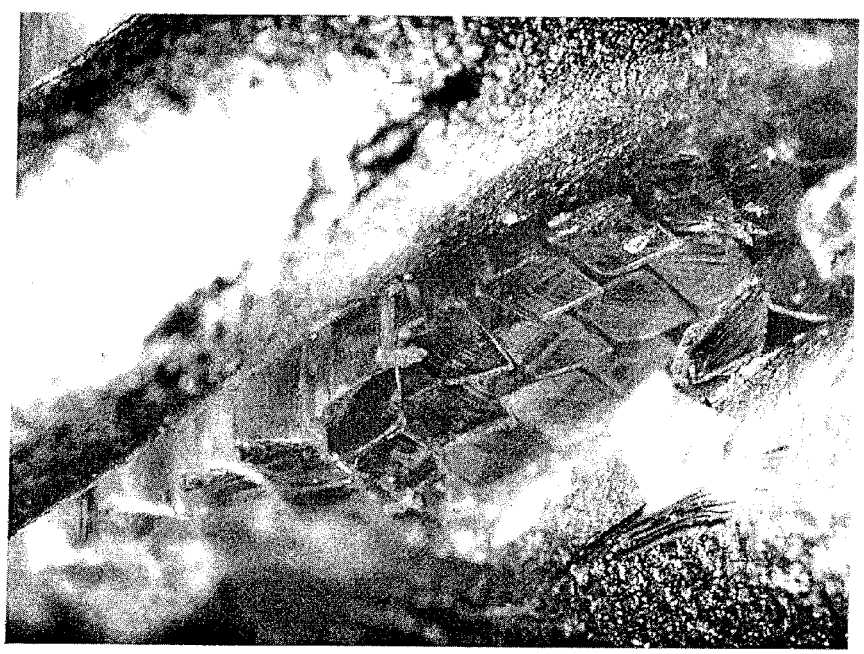

FIGS. 8A and 8B are enlarged photographs of the brush portion: FIG. 8A is an example of arranging filaments of approximately equilaterally triangular cross sections, and FIG. 8B is an example of arranging filaments of approximately rhombic cross sections. FIG. 8A shows that the filaments have a high filling density to leave no space therebetween, and that the acute corners of the filaments, although having mutually different acute angles, are all oriented in the axial direction of the brush portion, in the manner shown in FIG. 3. The rhombus case of FIG. 8B shows that the longer diagonal lines are all oriented in the axial direction of the brush portion, and that there is some degree of space in this sample, which can be easily addressed by further twisting the wire and thus increasing the filling density.

What is claimed is:

1. An interdental brush, comprising:
   a brush portion, the brush portion having a wire and filaments arranged therein by folding the wire and disposing the filaments between the wire and then twisting the wire,
   wherein the filaments each have a polygonal cross section;
   wherein at least one interior angle of the polygonal cross section has an acute angle of 30 to 75 degrees;
   wherein a twisting angle of the wire is 25 to 40 degrees, and
   wherein the polygonal cross sections of at least half of the filaments arranged in the brush portion are densely arranged.

2. The interdental brush according to claim 1, wherein the acute angle is larger than the twisting angle of the wire.

3. The interdental brush according to claim 1, wherein the acute angle is 1.2 to 3 times the twisting angle of the wire.

4. The interdental brush according to claim 1, wherein the acute angle is 1.5 to 2.5 times the twisting angle of the wire.

5. The interdental brush according to claim 1, wherein the acute angle is 1.7 to 2.2 times the twisting angle of the wire.

6. The interdental brush according to claim 1, wherein the polygonal cross section is an approximately equilateral triangle.

7. The interdental brush according to claim 1, wherein the polygonal cross section is an approximate rhombus.

8. The interdental brush according to claim 1, wherein the polygonal cross section is an approximately isosceles triangle.

9. The interdental brush according to claim 1, wherein the polygonal cross section is an approximate parallelogram.

10. The interdental brush according to claim 1, wherein the acute angle constitutes at least one end of the longest side of the polygonal cross section.

11. The interdental brush according to claim 1, wherein two or more rows of the filaments between the wire are laminated in the axial direction of the brush portion.

12. The interdental brush according to claim 1, wherein at least half of the filaments between the wire are laminated with their polygonal cross sections in a densely arranged state.

13. The interdental brush according to claim 1, wherein an orientation of an acute corner portion of the acute angle of the polygonal cross section of the filament, which is viewed from a center of gravity, is approximately equal or close to an axial direction of the brush portion, when the filaments are disposed between the wire.

14. The interdental brush according to claim 1, wherein the polygonal cross sections of the filaments are densely arranged without spaces.

15. The interdental brush according to claim 1,
   wherein two or more rows of the filaments between the wire are laminated in the axial direction of the brush portion, and
   wherein pairs of said two or more rows of the filaments between the wire are arranged such that their cross-sections are mirror-images, and individual rows of said pairs of said two or more rows of the filaments between the wire are in contact with each other.

16. The interdental brush according to claim 1,
   wherein at least four rows of the filaments between the wire are laminated in the axial direction of the brush portion,
   wherein first and second rows of said at least four rows of the filaments between the wire are arranged such that their cross-sections are mirror-images, and said first and second rows of the filaments between the wire are in contact with each other,
   wherein third and fourth rows of said at least four rows of the filaments between the wire are arranged such that their cross-sections are mirror-images, and said third and fourth rows of the filaments between the wire are in contact with each other, and
   wherein said third and fourth rows of said at least four rows are stacked on top of said first and second rows of said at least four rows.

17. The interdental brush according to claim 1,
wherein said filaments have a rhombus or parallelogram shape, and at least one row of the filaments between the wire is disposed in the axial direction of the brush portion, and
wherein individual filaments of said at least one row of the filaments between the wire are in contact with each other.

18. The interdental brush according to claim 1,
wherein said filaments have a rhombus or parallelogram shape, and at least two rows of the filaments between the wire are laminated in the axial direction of the brush portion,
wherein individual filaments of said at least two rows of the filaments between the wire are in contact with each other, and
wherein one row of said at least two rows is stacked on top of another row of said at least two rows.

* * * * *